United States Patent [19]

Gorman et al.

[11] Patent Number: 4,820,306

[45] Date of Patent: Apr. 11, 1989

[54] METHOD FOR AUGMENTATION OF THE ALVEOLAR RIDGE

[75] Inventors: William G. Gorman, East Greenbush; David A. Byron, Bethlehem, both of N.Y.

[73] Assignee: Sterling Drug Inc., New York, N.Y.

[21] Appl. No.: 573,262

[22] Filed: Jan. 23, 1984

Related U.S. Application Data

[60] Division of Ser. No. 379,779, May 19, 1982, Pat. No. 4,551,135, which is a continuation-in-part of Ser. No. 275,861, Jun. 22, 1981, abandoned.

[51] Int. Cl.[4] ................................................ A61F 2/00
[52] U.S. Cl. ...................................... 623/16; 623/66; 433/81; 433/201.1
[58] Field of Search .......................... 604/4, 54, 57–61, 604/82, 84, 89–92, 218–223, 226–229, 231, 236, 238, 256, 259, 416; 128/92 G, 92 C, 92 R, 92 A, 1 R; 3/1.9; 34141/27; 433/80, 81, 89, 90, 201.1, 215, 217.1; 425/DIG. 11; 264/16

[56] References Cited

U.S. PATENT DOCUMENTS

| | | | |
|---|---|---|---|
| 375,427 | 12/1887 | Richards | 433/81 |
| 3,112,743 | 12/1963 | Cochran et al. | 128/92 C |
| 3,227,161 | 1/1966 | De Lorenzo | 604/58 |
| 4,046,145 | 9/1977 | Choksi et al. | |
| 4,060,082 | 11/1977 | Lindberg et al. | |
| 4,195,366 | 4/1980 | Jarcho et al. | 128/92 C |

FOREIGN PATENT DOCUMENTS 0026090  1/1981  European Pat. Off. ............ 433/201

OTHER PUBLICATIONS

"Corr. of Hyper. Rdg. with Use of Hydroxylapatite"; *Dental Abst.;* vol. 29, No. 9; 9/1984; p. 470; Larsen et al.
"Ost. of Ap. Cer. in Dog's Mand.;" Aoki et al.; *Chemical Abstracts,* vol. 88; 1978; 88:177178g.
"In vio Sur. Act. of a Hydro. Alv. Bone Sub.", Ducheyne et al.; *Journal of Bio. Mat. Res.*; vol. 15, pp. 441–445, 5/1981.
"Syn. Hydro. Imp. in Bone"; Takahashi et al.; *Chemical Abstracts,* vol. 94; 1981; 94:127339p.
"Biocom. of Apa. Cer. in Mand."; Kato et al.; *Biomat. Med. Dev. Art.* Org.; vol. 7(2); pp. 291–297; Aug. 1979.

*Primary Examiner*—Richard J. Apley
*Assistant Examiner*—Alan W. Cannon
*Attorney, Agent, or Firm*—William G. Webb; Paul E. Dupont

[57] ABSTRACT

The invention comprises a syringe for extrusion of a semi-plastic mass, or a mass having a paste-like consistency. In a preferred embodiment, the syringe is so-designed to permit mixing of two components of a plasticizable mixture within the syringe barrel. The bore of the syringe barrel is flared to facilitate extrusion of the plastic mass therefrom. The parts of the syringe ready for use are packaged in a one-piece tray which serves not only for shipping and storing of the syringe, which may be preloaded with one of the components of the plasticizable mixture, together with the associated syringe parts, but which also serves, when opened for use, as a convenient tray for handling the syringe while mixing the two components of the plasticizable mixture prior to extrusion.

29 Claims, 2 Drawing Sheets

METHOD FOR AUGMENTATION OF THE ALVEOLAR RIDGE

CROSS REFERENCE TO RELATED APPLICATIONS

This is a division of our prior, co-pending application Ser. No 379,779, filed May 19, 1982, U.S. Pat. No. 4,551,135 which is a continuation-in-part of our prior application Ser. No. 275,861, filed June 22, 1981, now abandoned.

BACKGROUND OF THE INVENTION (a) Field of the Invention

This invention relates to syringes useful in extruding a semi-plastic mass, or a mass having paste-like consistency, therefrom.

(b) Description of the Prior Art

The use of two component mixing syringes for dissolving a solid medicament in a liquid diluent prior to injection of the solution is well known in medical practice. An example of such syringes is illustrated by Lindberg et al. U.S. Pat. No. 4,060,082, which describes a syringe combination comprising a mixer/dispenser syringe, usually containing a solid medicament, which is connected via a collapsible connecting sleeve to a carrier syringe, usually containing a liquid diluent used to dissolve the medicament in the mixer/dispenser section. When it is desired to use the syringe, the two syringe sections are telescoped together thus forcing a fill needle positioned between the two syringe sections to make a communicating connection between the mixer/dispenser and the carrier syringe sections. The liquid contents of the carrier section can then be ejected through the fill needle into the mixer/dispenser section. After the solid medicament has dissolved, a hypodermic needle is attached to the exit end of the mixer/dispenser section, a plunger is attached to a rubber piston closing the other end, and the liquid contents can then be ejected.

There are various means for making connection between two sections of a two component mixing syringe, the collapsible sleeve and filling needle described in the abovenoted Lindberg et al. patent being one such mean. Another means of achieving such inter-connection is illustrated in Choksi et al. U.S. Pat. No. 4,046,145 which describes a LUER® lock/LUER® joint two-part unit.

However, syringes for dispensing liquids are difficult to use in the extrusion of semi-plastic masses, and may in some cases be inoperative for such purpose. While the prior art is thus instructive on the problem of mixing two components and dispensing a resulting solution in liquid form, so far as is known, the art is silent on the problem of mixing two or more components within a syringe barrel, so as to form a semi-plastic mass, or extrusion of a semiplastic mass from a syringe system.

BRIEF SUMMARY OF THE INVENTION

The present invention is directed to a dispensing syringe useful for extruding a semi-plastic mass therefrom which comprises a barrel, which may be preloaded with a semi-plastic mass or with one component of a multi-component plasticizable mixture, and which may be fitted at its lower or exit end with removable means for making inter-connection with a filling syringe used to add to the dispensing syringe a second component of the plasticizable mixture, and which is provided at its upper end with a slidable piston which is provided with means for making positive engagement with a plunger rod, the syringe being optionally provided with means to permit escape of air from the barrel thereof when the syringe is being filled with a second component from a filling syringe, the bore of the barrel of the dispensing syringe being flared from its upper end to its lower end in order to facilitate extrusion of the semi-plastic mass from the barrel.

More specifically, the invention is directed to the dispensing syringe in an end use configuration comprising a barrel flared toward its lower end, as described above, and containing a multi-component plasticized mass, a slidable piston within the bore of said barrel and a plunger rod inter-engaged with the piston.

A further aspect of the invention is directed to a plastic tray package having a cover sheet sealed over the top thereof and containing therein a combination of the dispensing syringe comprising a barrel, which may be preloaded with a semi-plastic mass or with one component of a multi-component plasticizable mixture, and which may be fitted at its lower end with removable means for making inter-connection with a filling syringe, the barrel being provided at its upper end with a piston slidable within the bore of the syringe barrel and a plunger rod with means for making positive inter-engagement with the piston, the barrel of the syringe being flared from its upper to its lower end to facilitate extrusion therefrom of the plasticized mass.

BRIEF DESCRIPTION OF THE DRAWINGS

In order to fully describe the invention herein and the manner of using it, it will be necessary to use certain portions of a syringe unit as points of reference to illustrate relative movements of the parts of the syringe. Therefore, throughout this specification and in the appended claims, the terms "lower" and "downwards" are intended to refer to the exit end of the syringe and its various associated parts as assembled or oriented in the syringe for extruding use, and the terms "upper" and "upward" are intended to refer to the opposite or head end of the same.

The invention is described hereinbelow with reference to the accompanying drawings wherein.

DETAILED DESCRIPTION OF THE INVENTION

The invention will now be described in detail with reference to the foregoing figures where like numerals are used to designate like parts.

Figure 1:
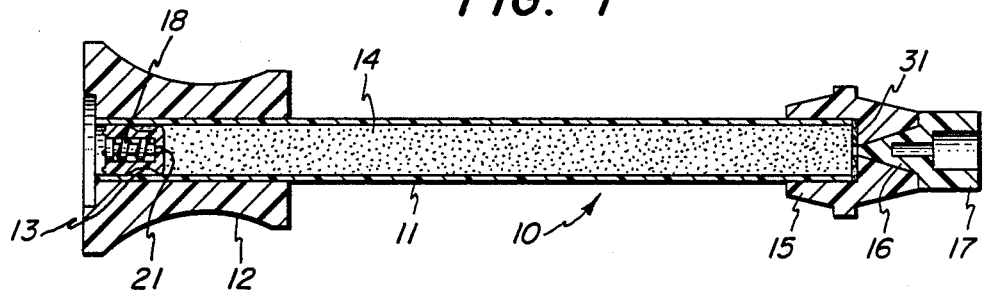
FIG. 1 is a longitudinal section view of a mixing/dispensing syringe unit of the invention in a pre-use configuration when pre-loaded with one component of a plasticizable mixture.
Figure 2:
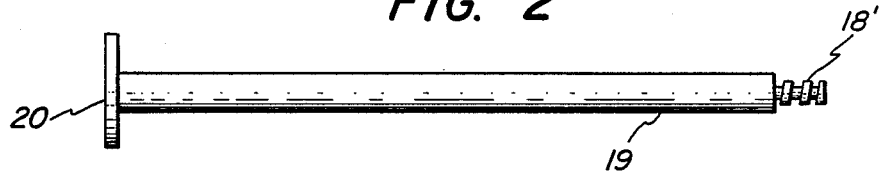
FIG. 2 is a plan view of a plunger rod used in combination with a dispensing syringe of the invention.
Figure 5:
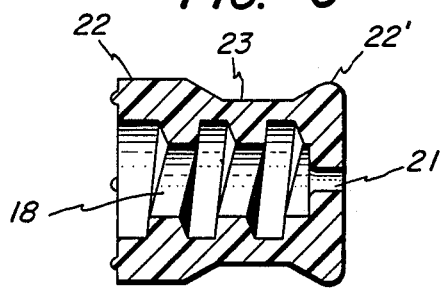
FIG. 5 is an enlarged view in transverse section of a slidable piston used within the barrel of the mixing/dispensing syringes of the invention.

FIG. 1 illustrates, in pre-use configuration, a mixing/dispensing syringe, generally indicated by reference numeral 10, for use in extruding a semi-plastic mass, or a mass of paste-like consistency, which comprises a barrel 11 having at the upper end thereof a finger grip 12 and closed at the same end by a slidable piston 13. The barrel is filled with a solid, or particulate, component 14 of a plasticizable mixture, which on admixture with a liquid component forms a semi-plastic mass. In its pre-use configuration, the lower end of the barrel is fitted with an adapter 15 which is frictionally engaged with the end of the syringe barrel and which has a LUER ® taper joint 16 for receiving an optional mating closure plug 17. The slidable piston 13 has a threaded opening 18 for positive interengagement with the threaded end 18' of a plunger rod 19, shown in FIG. 2, having a thumb plate 20 at the upper end thereof. The slidable piston optionally has a vent hole 21, which is best seen in FIG. 5, and which serves a purpose which will now be described with reference to FIG. 3.

Figure 3:
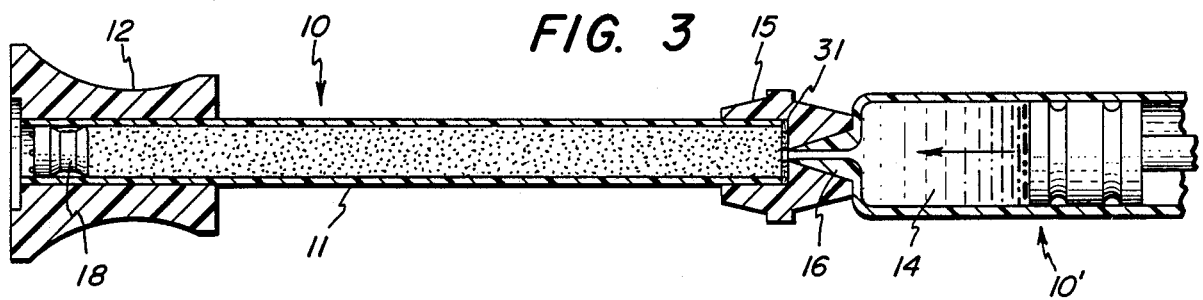
FIG. 3 is a fragmentary longitudinal section view depicting a mixing/dispensing syringe of the invention in combination with a filling syringe as the two would be configured in a loading or mixing combination.

As shown in FIG. 3, when it is desired to add a liquid component of the plasticizable mixture to the mixing syringe barrel 11, the closure plug 17 (if present) is removed, and a filling syringe 10' containing the liquid component 14' within the barrel thereof is attached to the mixing syringe 10 via LUER ® joint 16 in adapter 15. With the syringes thus joined, the contents of the filling syringe 10' are ejected into the barrel of the mixing syringe 10 where the liquid component 14' from syringe 10' surrounds and fills the interstices within the particulate material 14, the air within barrel 11 being expelled through vent hole 21 as barrel 11 is filled When the two components 14/14' have been thus admixed, the filling syringe 10' is detached from the adapter 15, and the closure plug 17 (if used) is reinserted into the LUER ® joint 16, thus restoring the syringe to the configuration shown in FIG. 1. The assembly is then maintained in this configuration until the plasticizable mixture sets up to the proper semi-plastic consistency and is thus ready for extrusion.

In an alternative means of filling the mixing syringe with a liquid component, the syringe barrel 10 would be only partially filled with the solid or particulate material 14, and the piston 13 would be positioned approximately midway in the syringe barrel. The plunger 19 would be connected to the piston via the screw-threaded attachment 18/18', the optional closure plug 17 would be removed from adapter 15, the end of the dispensing syringe with the attached adapter would be immersed in a container holding the desired liquid component, and the plunger/piston would be withdrawn so as to raw the liquid into the syringe barrel for admixture with the solid component 14. The closure plug 17 can then, if desired, be reinserted in adapter 15 until the unit is ready for use. When the syringe is filled in this manner with the liquid component, it is clear that the vent hole 21 in the piston is not essential.

Figure 4:
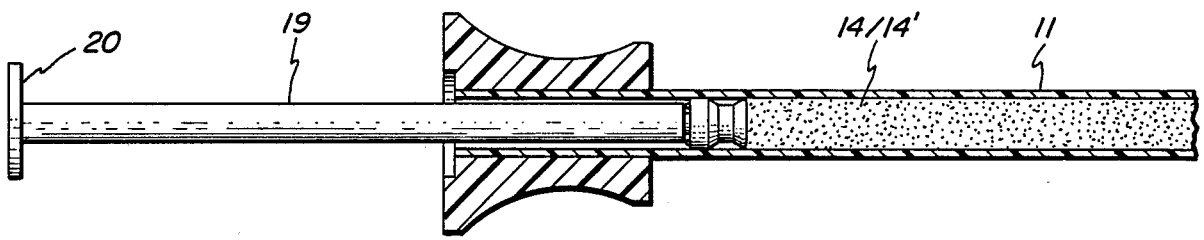
FIG. 4 is a fragmentary longitudinal view in partial section of a dispensing syringe of the invention as configured during use to extrude a semi-plastic mass from the barrel thereof.

After filling the syringe with the liquid component as described above, use of the assembly thereafter is seen with reference to FIG. 4. Thus when it is desired to extrude the semi-plastic mass from the dispensing syringe barrel, the plunger rod 19 is engaged with the piston 13 via threaded connection 18/18', thus sealing vent hole 21 if present, the adapter/closure plug section 15/17 is removed from the end of the barrel, and the semi-plastic mass is forced from the barrel by downward pressure on thumb plate 20 of plunger 19.

Extrusion of the mass from the barrel is facilitated by providing the bore of the barrel with a slight flare (see FIG. 3) from the upper end to the lower, or exit, end thereof. The amount of flare necessary to achieve this purpose would not be discernible in the drawings illustrating the invention, but desirably such flare, that is the difference in the inside diameters between the upper and lower ends of the barrel, should be around 0.015 inches to 0.050 inches over a typical barrel length of around 3 to 4 inches. A particularly preferred amount of flare is 0.025 inches over a length of about 3.5 inches.

Extrusion of the semi-plastic mass is further facilitated by use of a piston of appropriate design and dimensions. A suitable piston is depicted in FIG. 5. In order to insure a proper seal between the piston and the inside wall of the barrel along its entire length, while not creating so much frictional drag as to render the piston inoperative, the piston is preferably molded with one or more annular shoulders, or sections of enlarged diameter, for example one shoulder 22 at the upper end of the piston and a second shoulder 22' at the lower end thereof. Both of these shoulders make sealing engagement with the inside barrel wall, while a section of diminished diameter 23 makes no frictional contact therewith.

The piston is made of a flexible, or easily compressible, material such as a natural or synthetic elastomer or rubber, for example vinyl rubbers or butyl rubbers, including brominated or chlorinated butyl rubbers, or neoprene. The diameter of the shoulders 22/22' is slightly larger than the greatest inside diameter of the barrel 11, but the shoulders are compressible to the smaller diameter of the barrel while the piston is at the upper end of the barrel before use. Owing to the resiliency of the piston, the shoulders thus expand as the piston slides along the barrel towards the lower or exit end.

Although a piston with two shoulders 22/22' has been depicted in the accompanying drawings, it is to be understood that such double shouldered piston has been chosen solely for the purpose of illustration, and pistons having a single shoulder, or any multiple number of shoulders, are contemplated as being within the purview of the invention. For example, a piston configured as shown in FIG. 5, but lacking shoulder 22, would be fully operative in the practice of the invention and is considered to be within the ambit of the inventive concept.

Figure 6:
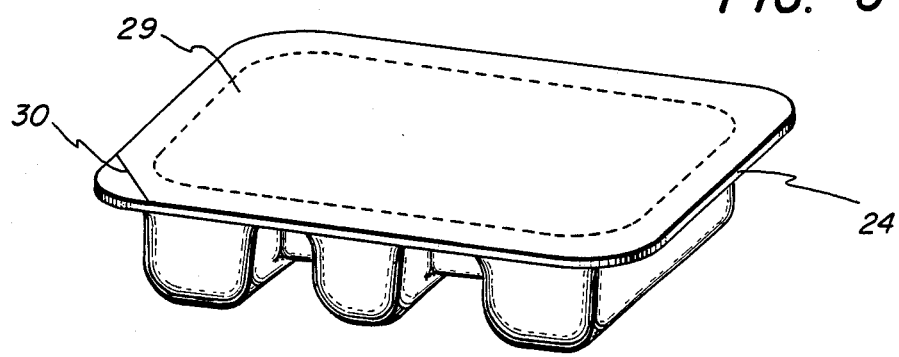
FIG. 6 is a perspective view of a package tray used to transport and store the syringe units of the invention.
Figure 7:
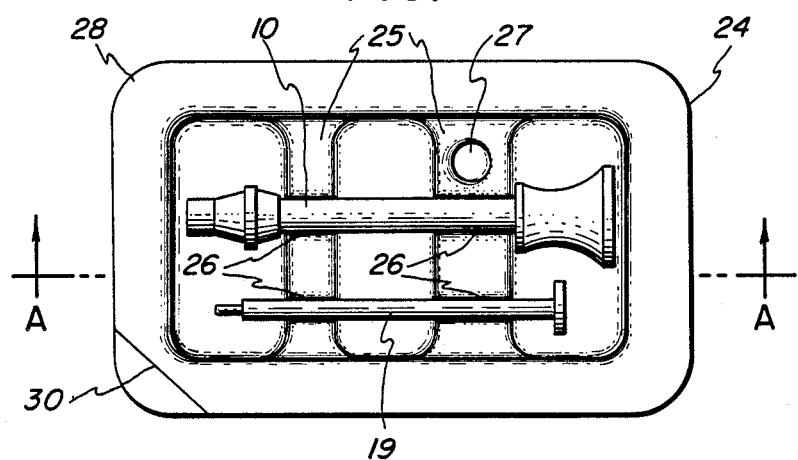
FIG. 7 is a top plan view of the package tray of FIG. 6 shown with the top cover of the tray removed and the mixing/dispensing syringe parts in position within the tray.
Figure 7A:
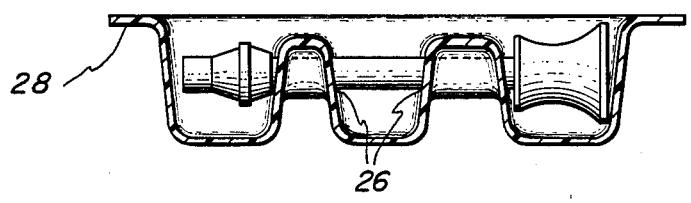
FIG. 7A is a section view on line A—A of FIG. 7.

The syringes of the invention, when pre-loaded with a solid component of a plasticizable mixture, can be prepackaged for shipment and storage in a package such as illustrated in FIGS. 6, 7 and 7A. The packages may consist of a thermoformed plastic tray 24 having two interior walls 25. The walls are formed with notches 26 which support the syringe body 10, together with its associated finger grip 12, adapter 15 and optional closure plug 17, and plunger rod 19. The tray can also be provided with a well 27 which can be used to temporarily store the closure plug 17 when the latter is removed either for direct filling of the syringe with the liquid component or for attachment of filling syringe 10' during the filling/admixing part of the use sequence all as described above. The tray is provided with a peripheral flange 28 to which a cover sheet 29, for example of Mylar or aluminum foil backed paper, can be affixed, for example, by heat sealing. A corner of the flange can be provided with a score line 30 to permit the corner of the tray to be broken off so as to provide a pull tab for peeling the cover sheet from the tray.

The syringes provided by the present invention find particular use in dispensing any multi-component semi-plastic mass including those prepared by addition of a liquid component to another component with which it can be admixed in the barrel, i.e. either another liquid component or a solid or particulate component. Such uses would include, for example, the extrusion of mixtures of fiber glass or powdered filler material with polyester resins, or two component glues such as resorcinol/formaldehyde glues.

The syringes of the invention are particularly useful in the field of dental surgery and especially in alveolar ridge augmentation procedures in edentulous patient. In such patients, over a period of time the alveolar ridge undergoes gradual bone resorption with consequent diminution in height of the alveolar ridge This process in turn produces a condition whereby dentures must be remolded and fitted to a continuously changing gum shape. The problem can be alleviated by restructuring the alveolar ridge with a material that is capable of bonding to tissue, is non-resorbable and provides a matrix for new bone growth. Materials which have been found useful for this purpose are certain ceramic materials, including especially hydroxylapatite and a mixture of hydroxylapatite and whitlockite. The process for preparing hydroxylapatite and whitlockite and the use of these materials as dental restoratives, as described above, are disclosed in U.S. Pat. Nos. 4,097,935 and 4,195,366, respectively.

In using syringes of the present invention in dental restorative procedures as described above, the barrel 11 of the syringe would be filled with the powdered ceramic material, i.e. hydroxylapatite, a mixture of hydroxylapatite and whitlockite or whitlockite alone. In one method of preparing the syringe for use, the dental surgeon would then use a separate blood sampling syringe 10' equipped with a detachable LUER ® needle/needle hub unit and withdraw a sample of the patient's blood from a vein. The needle/needle hub would then be removed from the blood sampling syringe, the closure plug 17 would be removed from the mixing/dispensing syringe unit 10, and the blood sampling syringe would then be attached via the adapter 15 to the mixing/dispensing syringe 10. The blood would then be ejected from one syringe into the other. The emptied blood sampling syringe would then be removed, the closure plug replaced, the plunger rod connected to the piston, the syringe containing the ceramic/blood mixture set aside, and the blood allowed to coagulate.

In a second method of preparing the syringe for use in dental restorative procedures, the plunger rod would be attached to the piston, the closure plug 17 (if present) would be removed from the adapter, and the end of the syringe with the attached adapter would be immersed in a container holding the desired liquid component, for example any physiologically inert liquid such as saline or glucose, and the liquid drawn up into the syringe barrel by drawing backwards on the plunger rod. The closure plug would then be reattached to the adapter and the whole assembly set aside until ready for use.

When used in the manner described above for dental restorative procedures, it will be apparent that reinsertion of the closure plug and attachment of the plunger rod, so as to close off the vent hole 21 if present, after the blood or other liquid component has been mixed with the ceramic material, effects a complete sealing of the syringe barrel thus protecting the contents from contamination.

Prior to preparation of the ceramic/blood coagulum or a ceramic/saline mixture as described above, the surgeon would intraorally prepare a mucoperiosteal tunnel through a vertical incision on the lateral aspect of the patient's jaw. The adapter/closure plug 15/17 would then be removed from the dispensing syringe, and the barrel of the syringe inserted through the incision and into the tunnel formed adjacent the alveolar ridge. By slowly withdrawing the syringe barrel while extruding the syringe contents by downward pressure on the plunger, the ceramic/blood mass would be deposited into the prepared mucoperiosteal tunnel adjacent the alveolar ridge. Ultimately the ceramic/blood mass will bond to the cortical bone thereby augmenting the alveolar ridge.

When used in alveolar ridge augmentation procedures as described above, the syringe barrel 11 can advantageously be supplied with appropriate indicia as an aid in determining the amount and the rate of extrusion of the plasticized material from the barrel.

Moreover, in the use of the syringes of the invention in alveolar ridge augmentation procedures, or in other uses in which the mixing/dispensing syringe barrel contains a particulate material, it is advantageous to employ an adapter unit 15 having a constricted opening into the barrel so as to miminize the possibility that the particulate material 14 would fall out of the barrel when the closure plug 17 is removed for attachment of the filling syringe 10' or for filling with a liquid component. Such constriction can be provided by means of a web 31, shown in FIGS. 1 and 3, having a narrow hole therethrough, across the throat of the LUER ® joint. The web can either be formed as a unitary section of adapter 15, or it can be provided as a separate part to the adapter.

Moreover, it is also contemplated that the dispensing syringes of the invention can be used in combination with attachments to effect a measured and predetermined extrusion rate of the contents. In one such means so contemplated, the syringe, containing a plasticized solid/liquid mixture and fitted with the plunger, would be detachably secured to a syringe holder having a trigger-operated ratchetting interconnection means with the plunger rod, much the same as well known household caulking guns. Thus with each squeeze on the trigger, the plunger rod/piston would be advanced at a known and predetermined rate which could be indexed to indicia on the syringe barrel as described above.

The syringes of the invention are suitably made of an appropriate plastic material which, when used in dental restorative processes, can be sterilized by autoclaving, gas or radiation. Thus the barrel, finger grip and closure plug can be made of polyethylene or polypropylene, while the plunger rod is suitably made of styrene or nylon. The adapter should preferably be made of a flexible material such as natural or synthetic elastomers or rubbers, for example vinyl or butyl rubbers, including brominated or chlorinated butyl rubber. The tray package is preferably made of any thermoplastic material such as polystyrene.

It will be understood that, although preferred embodiments have been described above in order to better illustrate the invention, alternative materials, forms and the like can be substituted for such aspects specifically described herein without either departing from the spirit of the invention or in any way adversely affecting the operability of the same.

For example, in the foregoing description, the means for venting air from the mixing/dispensing syringe barrel when used in combination with a filling syringe is illustrated as a hole 21 in piston 13. An alternative means of achieving the same result is the use of a ramp or wedge shaped section axially aligned with the syringe barrel and extending laterally along only a part of the inside periphery of the barrel at the upper end thereof. During the filling sequence, the piston would lie at the top of the ramp, and an air passage between the piston and the syringe barrel would be provided along either side of the ramp walls which would then be sealed off when the piston is moved downwards slightly thus displacing the piston from the ramp.

Furthermore, the means for making positive interconnection between the plunger rod and the piston has been described herein, for purposes of illustration, in terms of a threaded connection 18/18'. However, any of various means well known in the art for making such inter-connection that would be operative for the stated purpose, are considered to be within the ambit of the invention. Such alternative means of effecting interconnection include, for example, a bayonet, or push-and-turn, connection, or a ball and socket connection in which a spheroid or elongate spheroid shape is used on the end of the plunger rod with a cavity of corresponding shape molded into the piston. These, and other similarly effective inter-connecting means, are thus the full equivalents of the threaded inter-connection specifically exemplified herein.

Moreover, the means for connecting filling syringe 10' to mixing/dispensing syringe 10 is illustrated in the foregoing description as a LUER® joint 16. The LUER® joint is a particularly preferred means for effecting connection between the two syringes when used in dental restorative processes, because blood sampling syringes are conventionally equipped with a needle/needle hub unit which is detachable via a LUER® joint. Thus blood sampling syringes so-equipped are readily adapted to the mixing/dispensing syringes of the invention for dental restorative use. However, other means of effecting inter-connection, for example by use of a non-tapered joint, are also contemplated.

Also the invention has been described with particular emphasis on the mixing of a two-component solid/liquid plasticizable mixture. However, it will be apparent that the features of the syringe provided by the invention will lend themselves to use with a preformed semi-plastic mass or to the mixing of any kind and number of components which, on admixture, form a semi-plastic mass, such as one solid with two or more liquids, or two or more liquids, one with the others.

It will also be appreciated that the mixing/dispensing syringe can also function solely as a dispensing syringe, so that the syringe can be marketed when pre-loaded with a semi-plastic mass. When used for such latter purpose, it will be obvious that the need for venting the barrel would be obviated.

Having thus described the invention and the advantages thereof, it is considered that the invention is to be broadly construed and limited only by the character of the following claims.

We claim:

1. A method of augmenting alveolar ridges in an edentulous patient, said method comprising the steps of: (1) providing a charge of particulate dental restorative material; (2) providing a physiologically compatible delivery liquid; (3) mixing said delivery liquid with said charge to form a wetted extrudable semi-plastic mass; (4) forming a mucoperiosteal tunnel on the lateral aspect of the patient's jaw adjacent the alveolar ridge; (5) depositing said wetted extrudable mass in said tunnel by extruding said mass from a barrel having a bore which is slightly flared from its upper to its lower end for facilitating extrusion by relieving frictional forces between said wettable mass and barrel during said depositing step.

2. The method of claim 1 wherein said flare is 0.015 to 0.05 inches over a barrel length of from 3 to 4 inches.

3. The method of claim 2 wherein said flare is 0.025 inches over a barrel length of about 3.5 inches.

4. The method of claim 1 wherein said delivery liquid is blood.

5. The method of claim 1 wherein said delivery liquid is saline.

6. The method of claim 1 wherein said mixing step is performed in said barrel.

7. The method of claim 1 wherein said particulate dental restorative is a ceramic material.

8. The method of claim 1 wherein said particulate dental restorative is a ceramic material.

9. The method of claim 2 wherein said particulate dental restorative is a ceramic material.

10. The method of claim 3 wherein said particulate dental restorative is a ceramic material.

11. The method of claim 4 wherein said particulate dental restorative is a ceramic material.

12. The method of claim 5 wherein said particulate dental restorative is a ceramic material.

13. The method of claim 6 wherein said particulate dental restorative is a ceramic material.

14. The method of claim 1 wherein said particulate dental restorative is hydroxylapatite.

15. The method of claim 1 wherein said particulate dental restorative is hydroxylapatite.

16. The method of claim 2 wherein said particulate dental restorative is hydroxylapatite.

17. The method of claim 3 wherein said particulate dental restorative is hydroxylapatite.

18. The method of claim 4 wherein said particulate dental restorative is hydroxylapatite.

19. The method of claim 5 wherein said particulate dental restorative is hydroxylapatite.

20. The method of claim 6 wherein said particulate dental restorative is hydroxylapatite.

21. The method of claim 1 wherein said particulate dental restorative is a mixture of hydroxylapatite and whitlockite.

22. The method of claim 1 wherein said particulate dental restorative is a mixture of hydroxylapatite and whitlockite.

23. The method of claim 2 wherein said particulate dental restorative is a mixture of hydroxylapatite and whitlockite.

24. The method of claim 3 wherein said particulate dental restorative is a mixture of hydroxylapatite and whitlockite.

25. The method of claim 5 wherein said particulate dental restorative is a mixture of hydroxylapatite and whitlockite.

26. The method of claim 6 wherein said particulate dental restorative is a mixture of hydroxylapatite and whitlockite.

27. A method of augmenting the alveolar ridge in an edentulous patient comprising the steps of: (1) providing a charge of particulate dental restorative material of hydroxylapatite, whitlockite or mixtures thereof; (2) providing a physiologically compatible delivery liquid; (3) mixing said delivery liquid with said charge to form a wetted extrudable semi-plastic mass; (4) forming a mucoperiosteal tunnel on the lateral aspect of the patient's jaw adjacent the alveolar ridge; (5) depositing said wetted mass in said tunnel by extruding it from a barrel having a bore which is slightly flared from its upper to its lower end.

28. The method of claim 27 further comprising the step of withdrawing the barrel from said tunnel while extruding said mass.

29. The method of claim 4 wherein said particulate dental restorative is a mixture of hydroxylapatite and whitlockite.

* * * * *